US011679232B2

(12) United States Patent
Epple (10) Patent No.: US 11,679,232 B2
(45) Date of Patent: Jun. 20, 2023

(54) FLUSHING SYSTEM (71) Applicant: CardioBridge GmbH, Hechingen (DE)

(72) Inventor: Klaus Epple, Rangendingen (DE)

(73) Assignee: CardioBridge GmbH, Hechingen (DE)

( * ) Notice: Subject to any disclaimer, the term of this patent is extended or adjusted under 35 U.S.C. 154(b) by 824 days.

(21) Appl. No.: 16/484,814

(22) PCT Filed: Jan. 17, 2018

(86) PCT No.: PCT/EP2018/051053
§ 371 (c)(1),
(2) Date: Aug. 8, 2019

(87) PCT Pub. No.: WO2018/145865
PCT Pub. Date: Aug. 16, 2018

(65) Prior Publication Data
US 2020/0023158 A1    Jan. 23, 2020

(30) Foreign Application Priority Data

Feb. 13, 2017 (DE) .................. 10 2017 102 829.3

(51) Int. Cl.
*A61M 25/00* (2006.01)
*B08B 9/032* (2006.01)
(Continued)

(52) U.S. Cl.
CPC ............ *A61M 25/00* (2013.01); *A61M 60/13* (2021.01); *A61M 60/226* (2021.01);
(Continued)

(58) Field of Classification Search
CPC ...... A61M 2025/0019; A61M 2209/10; A61M 25/00; A61M 5/14212; A61M 5/14232; A61M 5/14228; A61M 60/13; A61M 60/135; A61M 60/226; A61M 60/408; A61M 60/554; A61M 60/808; B08B 9/0321; F04B 43/12; F04B 43/1223;
(Continued)

(56) References Cited

U.S. PATENT DOCUMENTS 3,306,228 A * 2/1967 Drutchas ............... F04C 2/18
418/192
4,585,399 A * 4/1986 Baier .................. F04B 43/1253
417/477.12
(Continued)

FOREIGN PATENT DOCUMENTS

DE    31 32 790 A1    3/1983
DE    202 09 663 U1    10/2003
(Continued)

*Primary Examiner* — Quynh-Nhu H. Vu
(74) *Attorney, Agent, or Firm* — Aslan Law, P.C.

(57) ABSTRACT

A flushing system for a catheter, in particular for a catheter of a catheter pump, comprising a supply line having a pump section, a discharge line having a pump section and a pump, wherein the diameter of the pump section of the discharge line is smaller than the diameter of the pump section of the supply conduit, the pump interacts with the pump section of the supply line for supplying flushing fluid to the catheter, and the pump interacts with the pump section of the discharge line for discharging flushing fluid from the catheter.

20 Claims, 9 Drawing Sheets (51) Int. Cl.
*F04B 43/12* (2006.01)
*A61M 60/808* (2021.01)
*A61M 60/554* (2021.01)
*A61M 60/408* (2021.01)
*A61M 60/13* (2021.01)
*A61M 60/226* (2021.01)

(52) U.S. Cl.
CPC ........ *A61M 60/408* (2021.01); *A61M 60/554* (2021.01); *A61M 60/808* (2021.01); *B08B 9/0321* (2013.01); *F04B 43/1223* (2013.01); *A61M 2025/0019* (2013.01); *A61M 2205/502* (2013.01); *A61M 2209/10* (2013.01)

(58) Field of Classification Search
CPC .............. F04B 43/1253; F04B 43/1261; F04B 43/1276; F04B 43/1284; F04B 43/1292
See application file for complete search history.

(56) References Cited

U.S. PATENT DOCUMENTS

| | | | | |
|---|---|---|---|---|
| 4,681,129 A | * | 7/1987 | Juzi | F22B 37/227 137/154 |
| 4,976,590 A | * | 12/1990 | Baldwin | F04B 49/06 417/477.3 |
| 5,340,290 A | * | 8/1994 | Clemens | F04B 43/1292 417/477.1 |
| 5,628,731 A | * | 5/1997 | Dodge | A61M 1/77 417/474 |
| 6,585,692 B1 | * | 7/2003 | Worthen | A61F 7/123 604/113 |
| 6,659,976 B2 | * | 12/2003 | Beck | A61M 5/16854 604/246 |
| 6,852,094 B2 | * | 2/2005 | Beck | F04B 43/1253 604/246 |
| 7,070,575 B2 | * | 7/2006 | Beck | F04B 43/0072 604/246 |
| 8,377,001 B2 | * | 2/2013 | Pfouts | A61M 5/14232 417/477.2 |
| 9,642,965 B2 | * | 5/2017 | Marshall | A61M 5/142 |
| 9,907,901 B2 | * | 3/2018 | Orczy-Timko | A61M 1/72 |
| 2004/0022655 A1 | | 2/2004 | Knuth et al. | |
| 2005/0238515 A1 | * | 10/2005 | Kent | F04B 43/1292 417/474 |
| 2009/0053085 A1 | * | 2/2009 | Thompson | A61M 5/14232 417/477.2 |
| 2014/0135731 A1 | * | 5/2014 | Breitweiser | F04B 43/0072 604/151 |
| 2016/0331891 A1 | * | 11/2016 | Marshall | A61M 5/14228 |

FOREIGN PATENT DOCUMENTS

| | | |
|---|---|---|
| DE | 20 2009 018 145 U1 | 6/2011 |
| DE | 10 2010 031 793 A1 | 2/2012 |
| EP | 0 459 113 A1 | 12/1991 |
| EP | 0 711 570 A1 | 5/1996 |
| EP | 2 288 392 B1 | 3/2011 |
| JP | H09-308 686 A | 12/1997 |
| WO | WO 2009/055639 A2 | 4/2009 |
| WO | WO 2014/164136 A1 | 10/2014 |

* cited by examiner

FLUSHING SYSTEM

CROSS-REFERENCE TO RELATED APPLICATIONS

This application claims priority to German Patent Application No. 10 2017 102 829.3 filed on Feb. 13, 2017, and to PCT Application No. PCT/EP2018/051053 filed on Feb. 8, 2018, the entire contents of which are hereby incorporated by reference.

The invention relates to a flushing system for a catheter, in particular for a catheter of a catheter pump, comprising a supply line having a pump section, a discharge line having a pump section, and a pump. The invention also relates to an associated carrier element, an associated console and a catheter pump system.

A catheter pump is known from EP 2 288 392 B1, for example. The catheter pump has a drive unit and a catheter. The catheter comprises a pump head for insertion in particular into the arterial vascular system, such as the aorta or heart, and a rotatably mounted rotor shaft for driving an expandable conveying element provided on the pump head. A rotor that has fold-out propellers and is provided at the proximal end of the catheter can be used as the rotating conveying element.

Catheter pumps are inserted into the arterial vascular system, such as the aorta, of patients as a temporary circulatory support system, in particular when the natural heart is unable to provide the body with sufficient oxygenated blood. The conveying element and the rotor shaft are operated at comparatively high rotational speeds in the range of from 7,000 to 15,000 revolutions per minute, and in particular in the range of from 10,000 to 13,000 revolutions.

In order to prevent deposits forming in the catheter, to lubricate the catheter and in particular the rotor shaft rotating therein, and to prevent blood from entering the catheter, the catheter is flushed with flushing liquid. A flushing system is connected to the catheter for this purpose. A flushing system of this kind is already known from WO 2014/164136 A1, for example. In this case, a supply line for supplying flushing fluid and a discharge line for discharging flushing fluid are connected to the catheter. In order to achieve fluid conveyance in the supply line and discharge line, a rotary peristaltic pump is provided for the supply line and the discharge line in each case. The two pumps are actuated separately in this case in order to convey a corresponding amount of fluid into the catheter and conduct it out of the catheter, and to achieve a desired ratio of supplied to discharged fluid. This flushing system is both expensive and complex in design, because two pumps have to be provided, and complex to control or program, because the pumps have to be coordinated with one another.

The problem addressed by the present invention is therefore that of providing a flushing system for a catheter which remedies the above-mentioned disadvantages of the prior art.

This problem is solved by a flushing system having the features of claim 1. The diameter of the pump section of the discharge line is thus smaller than the diameter of the pump section of the supply line. Furthermore, the pump cooperates with the pump section of the supply line in order to supply flushing fluid to the catheter. Finally, the pump cooperates with the pump section of the discharge line in order to discharge flushing fluid from the catheter.

Consequently, there is only one pump, which is designed both to supply fluid into the catheter through the supply line and to discharge fluid out of the catheter through the discharge line. The fact that the diameter of the pump section of the discharge line is reduced compared with the diameter of the supply line means that the ratio of supplied fluid to discharged fluid can be set and adjusted without a second pump being required. In this case, the pump section of the discharge line cooperates with the pump in such a way that a kind of throttle point for the flushing fluid is formed. It can thus be achieved that approximately ⅔ of the flushing fluid pumped into the catheter remains in the body in which the catheter is located, and approximately ⅓ of the flushing fluid flows back through the catheter, and is discharged from the catheter by means of the discharge line.

The catheter may be the catheter of a catheter pump, as stated above. It may also be one of a wide range of other catheters, such as a catheter of a stent delivery system.

According to an advantageous development of the invention, the pump is designed as a peristaltic pump. In particular, the pump may be designed as a linear peristaltic pump. It is conceivable for the pump to have a camshaft having a number of cams, each cam being coupled in motion to a finger. Each finger cooperates with the supply line and the discharge line in order to convey fluid. In particular, the fingers sequentially compress the supply line and the discharge line to generate a fluid flow. The movement of the fingers results in the squashed pump section region also migrating such that a fluid flow is achieved. Overall, therefore, fluid can be supplied to the catheter and fluid can be discharged from the catheter by means of only one pump.

It is also advantageous for the pump sections to extend in parallel with one another and for flushing fluid to flow therethrough in opposite flow directions during operation. A flushing system of this kind has a particularly simple and compact design.

It is particularly preferred for a carrier element to be provided to which the supply line and the discharge line are fastened. The carrier element makes it possible to provide, in a particularly simple manner, an operative connection between the supply line and discharge line and the pump by the carrier element being suitably mounted in the pump region such that the pump sections of the supply line and discharge line can cooperate with the pump.

It is further particularly preferred for the carrier element to extend along a main extension plane. In this connection, it is conceivable for the supply line and discharge line to extend through the carrier element in said main extension plane. The carrier element is therefore particularly compact and can be connected in a particularly simple manner to a linear peristaltic pump.

It is further particularly preferred for the carrier element to have an opening, the pump sections of the supply line and discharge line extending along the opening and thus bridging it. It is conceivable for the fingers of the linear peristaltic pump to engage in the opening and to thus cooperate with the pump sections which bridge the opening.

Advantageously, the supply line and/or the discharge line have an arcuate section, the section extending through the carrier element such that the supply line and/or discharge line are guided into the carrier element and out of the carrier element on the same side of the carrier element. The supply and/or discharge line can thus be supplied to the carrier element on one carrier-element side and guided out of the carrier element on the same side. This is advantageous in that the two lines can be supplied by means of only one pump, and in particular by means of a linear peristaltic pump, such that the fluid is conveyed in the supply line for supplying and is conveyed in the other line for discharging.

It is also conceivable, however, for the supply and/or discharge line to be guided into or out of the carrier element on opposite sides.

It is further preferred for a console having the pump to be provided. In this case, the pump sections of the supply line and discharge line can be inserted into a receptacle in the console in such a way that the pump can cooperate with the pump sections in order to convey fluid. Thus, by inserting the pump sections into the console, an operative connection between the pump and the supply line and discharge line can be provided in order to convey fluid into and out of a catheter.

It is particularly preferred for the carrier element together with the supply line and discharge line to be detachably placeable on the console. In contrast with the console, the supply line and discharge line are wear items, since these usually have to be sterile. A new supply line and discharge line have to be used for each patient. In this respect, the supply line and discharge line can be replaced quickly by simply removing or rearranging the carrier element together with the supply line and discharge line on the console.

Advantageously, the console has a closing element for closing the receptacle, the pump sections cooperating with the pump in order to convey fluid only when the closing element assumes its closed position. In this context, it is conceivable for the closing element to have an operative section which is provided opposite the fingers of the linear peristaltic pump such that the pump sections are provided between the operative section and the fingers.

In this connection, a particularly preferred development of the invention results from the fact that the closing element has a pressing element which presses the supply line and/or the discharge line against the fingers under preloading. In this case, one or more spring elements can be provided in order to push the pressing element against the supply and/or discharge line. It is in particular conceivable for the pressing elements to be arranged opposite the fingers of a linear peristaltic pump such that the pressing elements exert a continuous force on the pump sections in the direction of the fingers, while the fingers sequentially apply a force to the pump sections in the direction of the pressing elements in order to generate a fluid flow.

The problem stated at the outset is also solved by a carrier element for a flushing system according to the invention, the supply line and the discharge line being fastened to the carrier element. This wear item can be fastened particularly easily and replaceably in particular to the console.

Furthermore, the problem stated at the outset is also solved by a console for a flushing system according to the invention, the console having a pump and a receptacle for the pump sections. The pump sections of the supply line and discharge line can be inserted into the receptacle in such a way that, after insertion, there is an operative connection between the pump and the pump sections in order to generate a fluid flow through the lines.

Finally, the problem stated at the outset is also solved by a catheter pump system. The catheter pump system in this case comprises a catheter pump having a catheter and a flushing system according to the invention, the supply line and the discharge line of the flushing system being fluidically connected to the catheter. The catheter of the catheter pump can be flushed in a particularly simple manner by means of the flushing system.

Further details and advantageous designs of the invention can be found in the following description, on the basis of which the embodiments of the invention shown in the drawings are explained and described in more detail. In the drawings.

Figure 1:
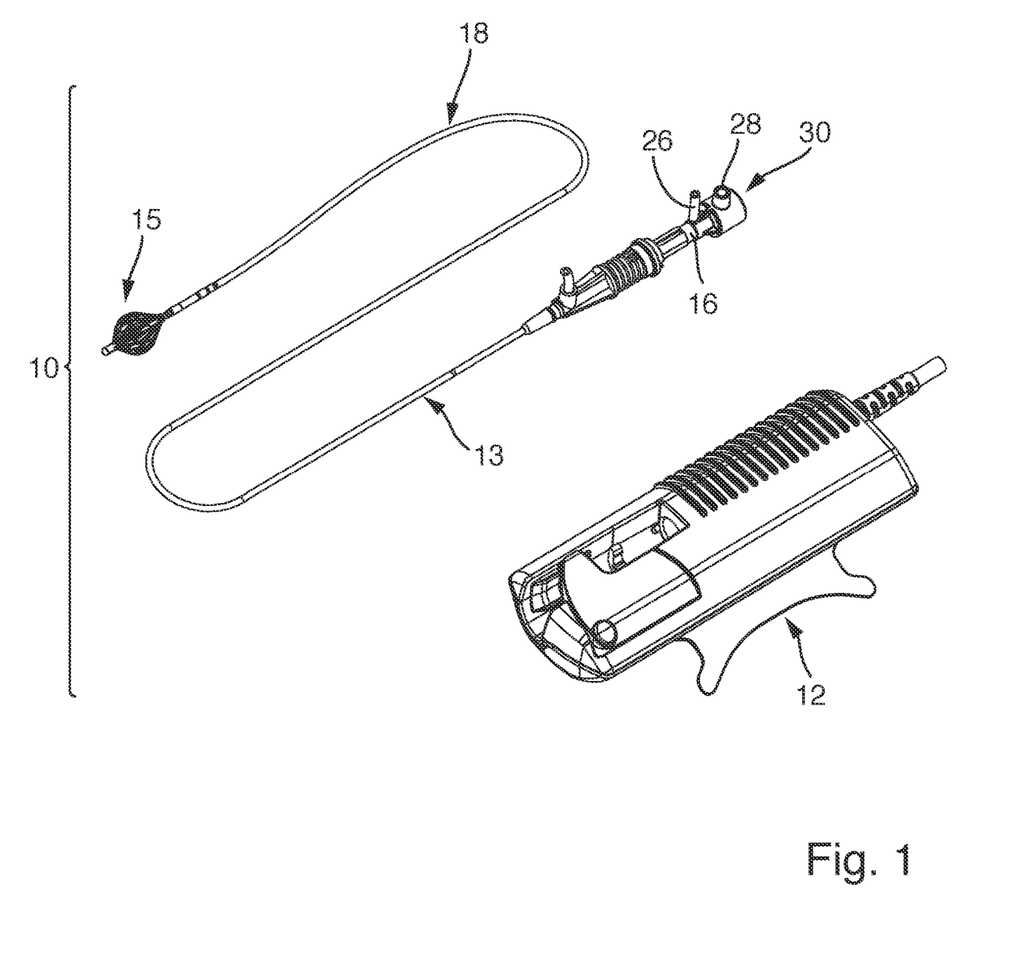
FIG. 1 shows a catheter pump with a drive unit and a catheter.
Figure 2:
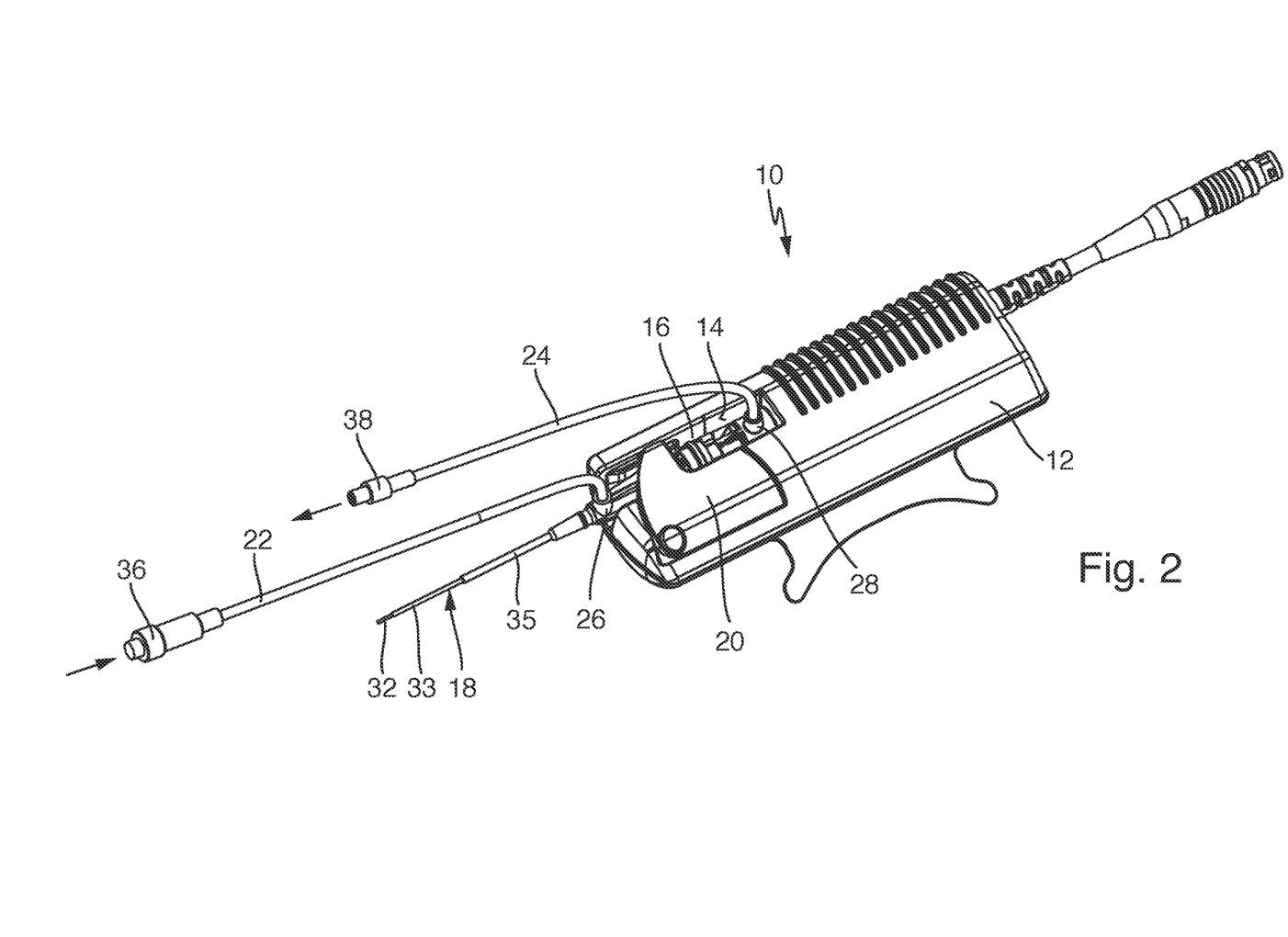
FIG. 2 shows a drive unit of a catheter pump in the operating position.

FIGS. 1 and 2 show a catheter pump 10 comprising a drive unit 12 and a catheter 18 that can be coupled to the drive unit 12. The catheter 18 has, at its distal end, a pump head 15 for insertion into the arterial vascular system, such as the aorta. The catheter 18 is designed to be inserted into the body of a mammal, such as a human, via the femoral artery and to be positioned for example in the aorta in order to support the circulation of the heart. The catheter 18 is relatively long, such that it can extend from the percutaneous insertion site in the femoral artery, for example, into the groin and up to the aortic arch.

A rotor shaft 32 is provided in the catheter 18, by means of which shaft a conveying element provided in the pump head 15, such as a rotor having fold-out propellers, can be rotated. The drive unit 12 has a receptacle 14. The proximal end 16 of the catheter 18 is arranged in the receptacle 14 and is securely held there by means of a holding element 20. At its proximal end 16, the catheter 18 provides a coupling section 30 which can be placed into the drive unit 12, by means of which ultimately the rotor shaft 32, and thus the conveying element, is rotated.

Furthermore, two tubes 22, 24 are provided at the distal end 16. Flushing fluid can be introduced into the catheter 18 by means of the tube 22 via an inlet 26. Said flushing fluid is conducted through the catheter 18 to the pump head 15. In the pump head 15, some of this flushing fluid is guided back through the catheter 18 and discharged via an outlet 28 and the tube 24. In this process, the recirculated flushing fluid is guided back between the rotor shaft 32 that rotates during operation and an inner catheter 33. The inner catheter 33 is surrounded by an outer catheter 35, with flushing fluid being conveyed via the lumen between the inner catheter 33 and the outer catheter 35 toward the pump head 15.

Figure 3:
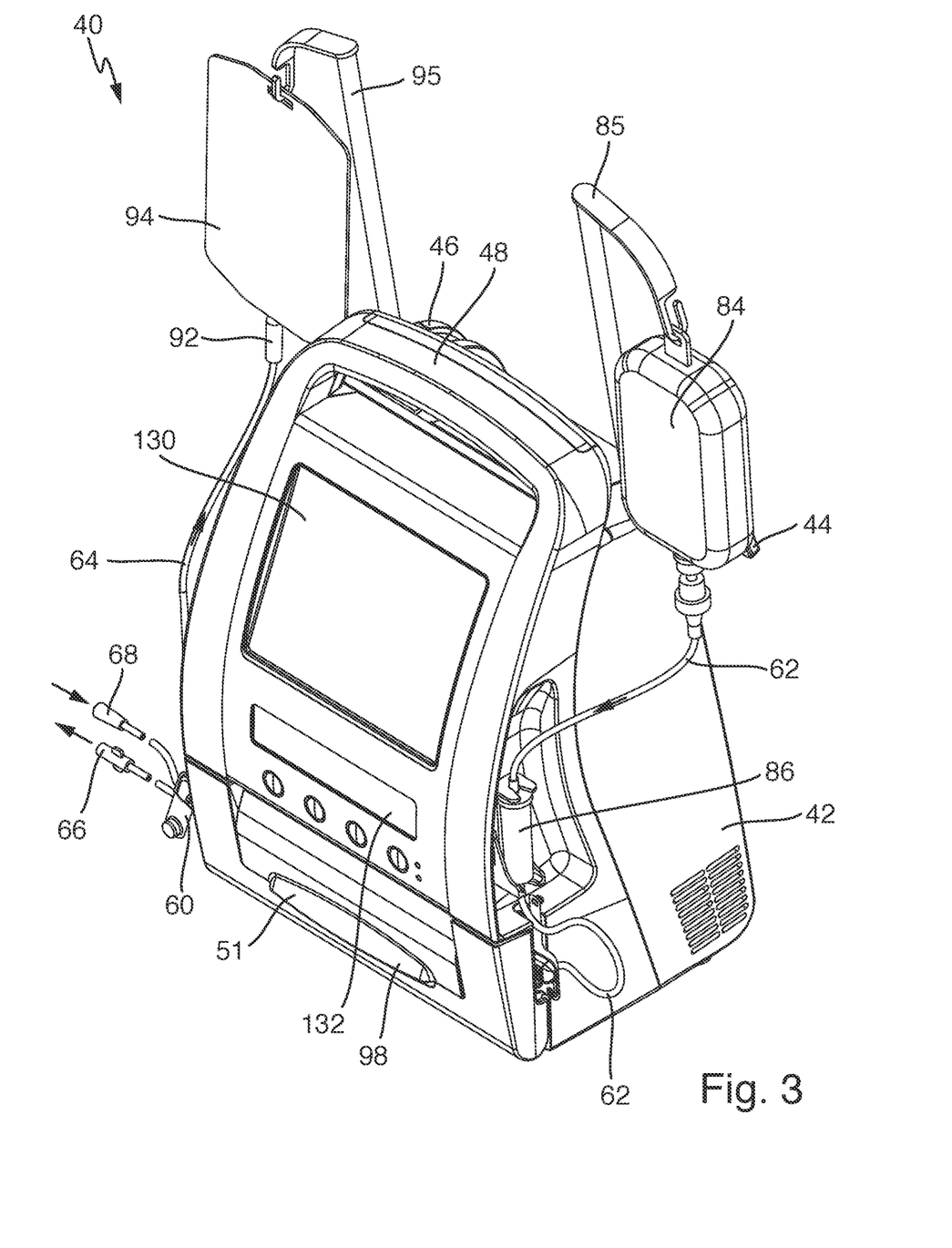
FIG. 3 is a perspective view of a console of a flushing system according to the invention with a carrier element fastened thereto and a closing element in the closed position.
Figure 4:
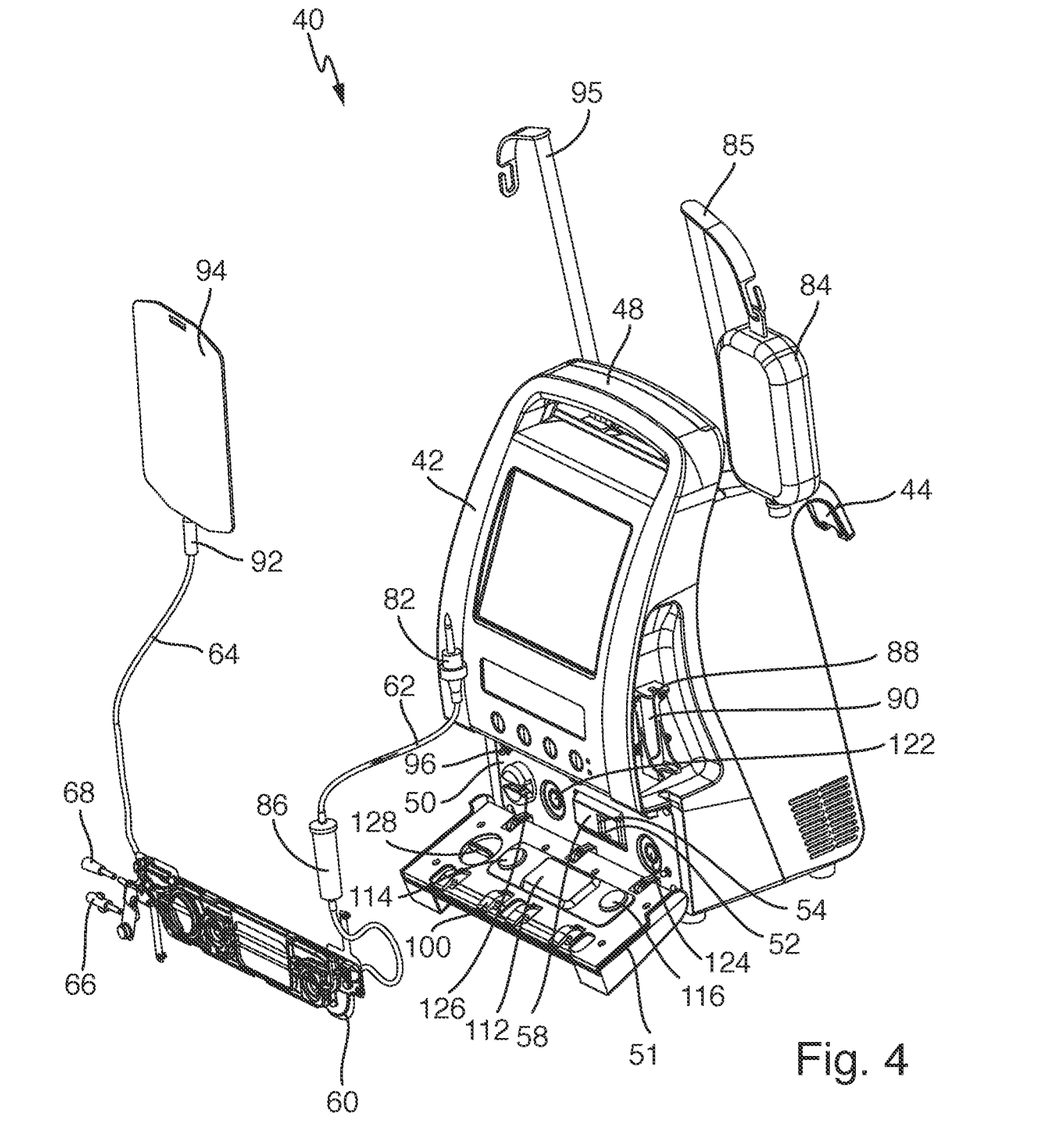
FIG. 4 is a view according to FIG. 3 with the closing element in the open position, the carrier element being detached from the console.

The tubes 22, 24 each have a connector piece 36, 38. Said connector pieces 36, 38 can be connected to a flushing system, which will be described in more detail below. The flushing system is shown in FIGS. 3 and 4 and denoted as a whole by reference numeral 40. First, the flushing system 40 comprises a console 42. Said console comprises two hooks 44, 46 on its rear side, by means of which the console can be fastened to a hospital bed, for example. The console 42 further comprises a holding section 48 so that the console 42 can be conveniently carried by an operator. The console further comprises a receptacle 50, which can be seen in FIG. 4, which can be closed by a pivotable closing element 51.

Furthermore, the console 42 comprises a pump 52 designed as a linear peristaltic pump. This pump 52 will be described in more detail below with reference to FIGS. 4 and 7: First, the pump 52 comprises a camshaft 56 having a number of cams (not shown). The cams are each coupled in motion to a finger 54. Said fingers 54 move in the radial direction, i.e. perpendicularly to the axis of rotation of the camshaft 56. The fingers 54 move in this case sequentially, i.e., collectively, the fingers 54 move together in a wave-like manner. FIG. 4 shows the fingers, which protrude into the receptacle 50 and are covered by a cover 58. A carrier element 60 can be arranged in the receptacle 50 and has a supply line 62 and a discharge line 64.

The carrier element 60 and the lines 62, 64 are described in more detail below with reference to FIGS. 3 to 6. First, the supply line 62 comprises a connector piece 66, while the discharge line 64 comprises a connector piece 68. The connector piece 66 can in this case be connected to the connector piece 36 of the tube 22 of the catheter pump 10 (cf. FIG. 2). The connector pieces 66 and 36 may form a Luer connection. Likewise, the connector piece 68 of the discharge line 64 can be connected to the connector piece 38 of the tube 24 of the catheter pump 10. The connector pieces 38 and 68 may also form a Luer connection.

Figures 5, 5A:
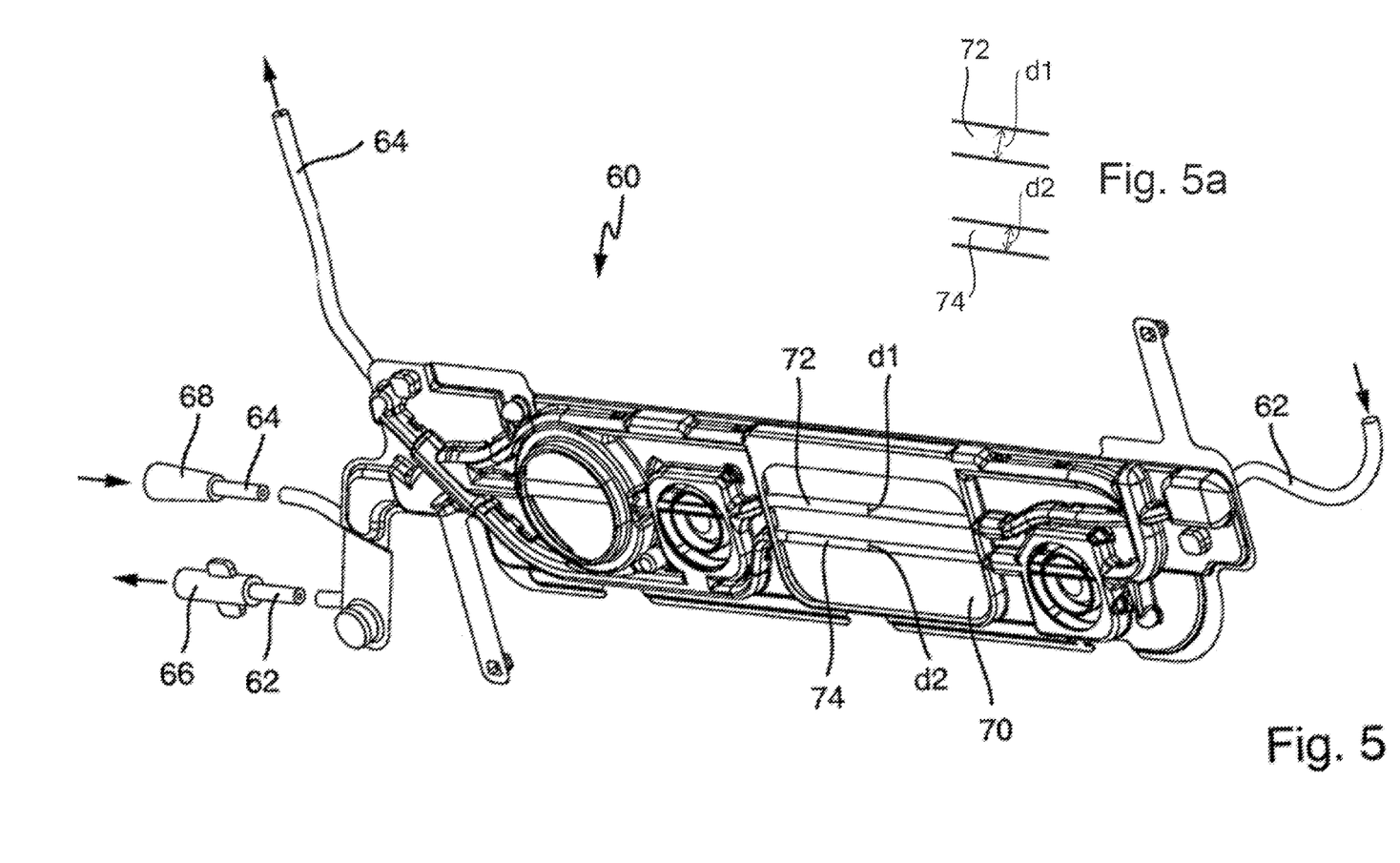
FIG. 5 is a perspective view of the carrier element shown in FIGS. 3 and 4.
FIG. 5a illustrates a diameter d2 of the discharge line pump section of the discharge line being smaller than a diameter d1 of the supply line pump section of the supply line.
Figure 5:
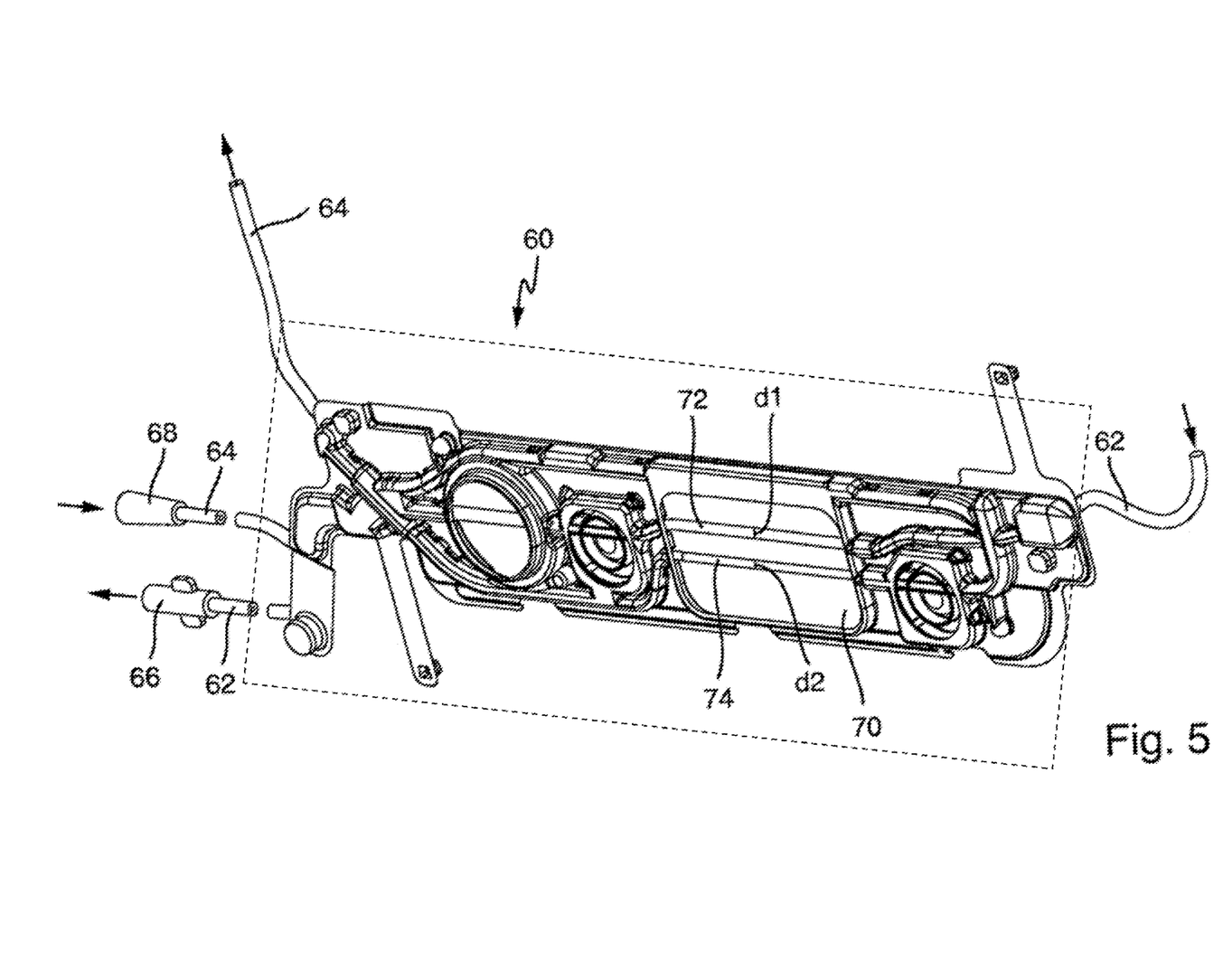
Figure 6:
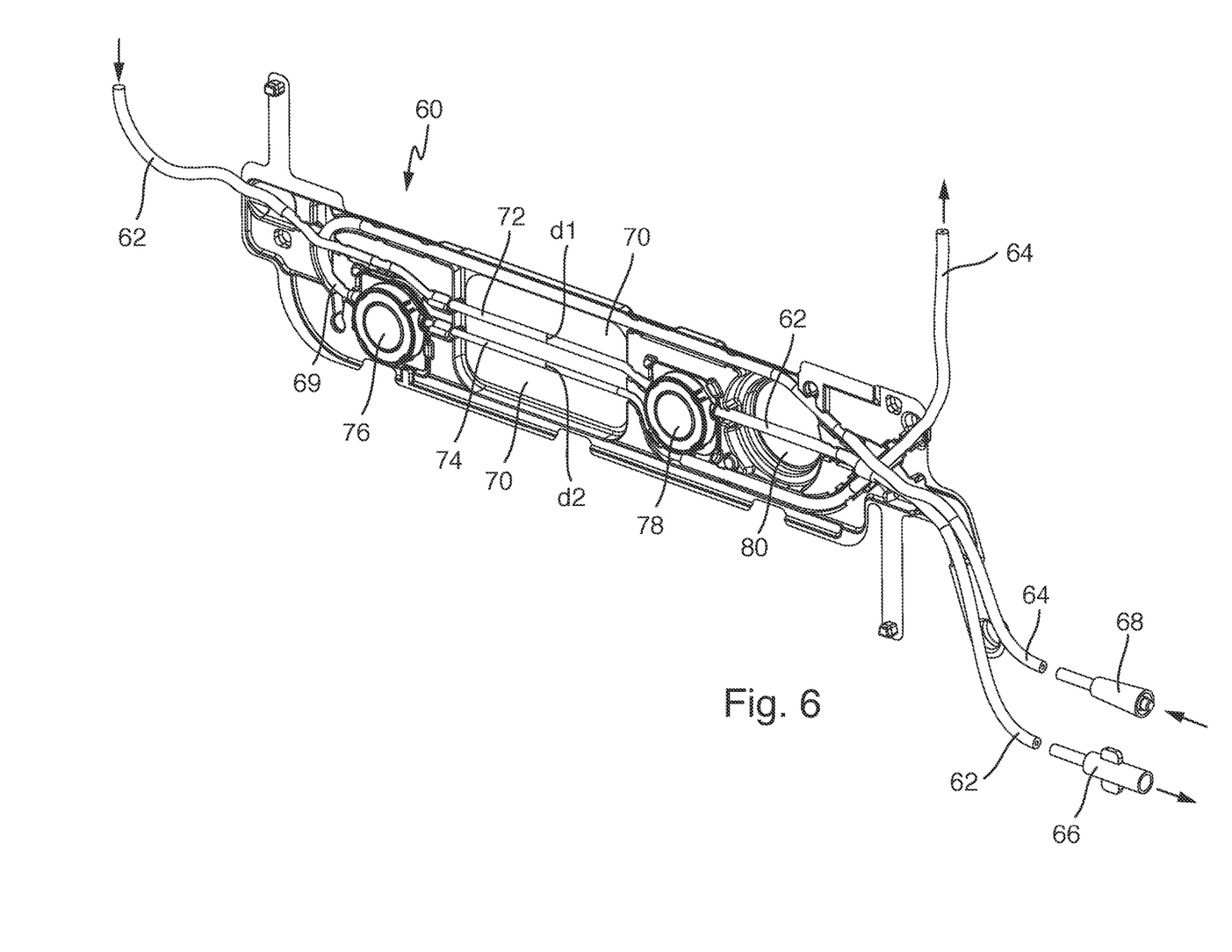
FIG. 6 is a further perspective view of the carrier element shown in FIGS. 3 and 4.
Figure 7A:
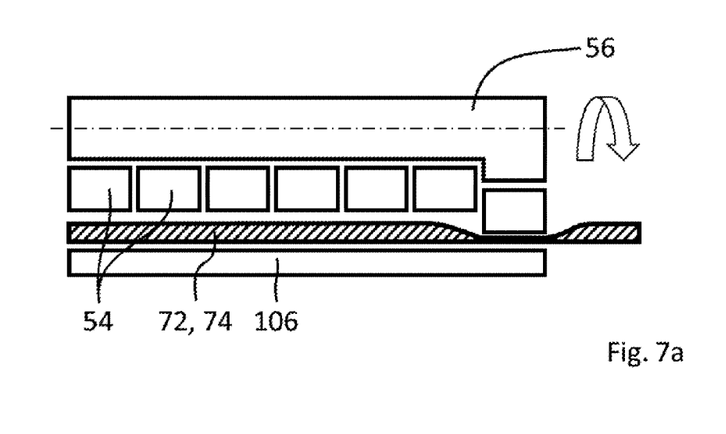
FIG. 7 is a schematic perspective view of a pump of the console shown in FIGS. 3 and 4.
Figure 7B:
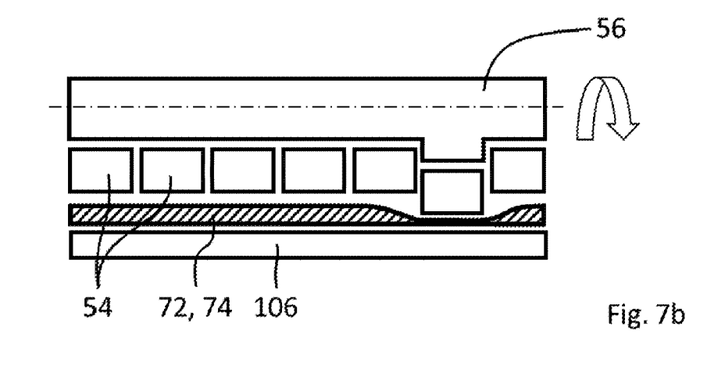
Figure 7C:
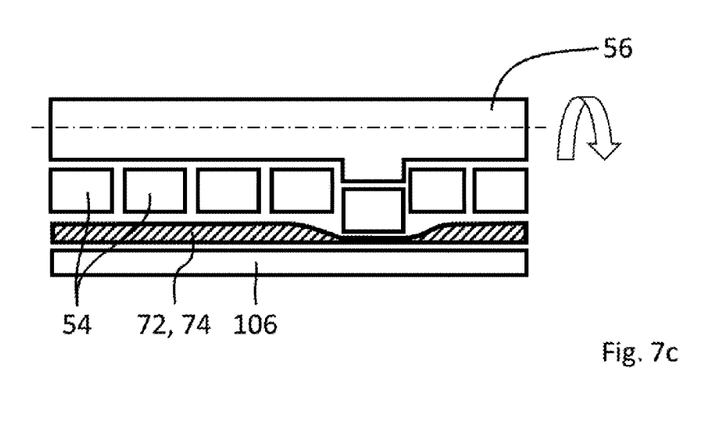
Figure 7D:
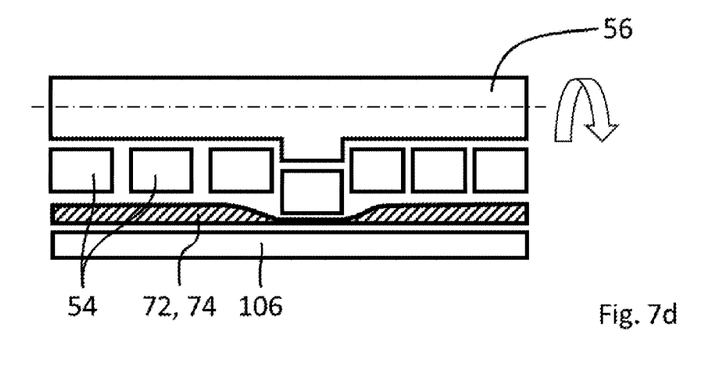

As can be seen clearly in FIGS. 5 and 6, the carrier element 60 extends in a main extension plane and has a modular design. The carrier element 60 is made of PET and is produced by plastic deep drawing or injection molding. The supply line 62 and the discharge line 64 are fastened to the carrier element 60 or extend through the carrier element 60. The carrier element 60 has channels for this purpose, in which the lines 62, 64 are guided. In the central region, the carrier element 60 has a rectangular opening 70. The lines 62, 64 extend along this opening 70 and bridge it.

The supply line 62 comprises a pump section 72 in the region of the opening 70. At the same time, the discharge line 64 comprises a pump section 74. The pump section 72 has a diameter d1, while the pump section 74 has a diameter d2. The diameter d1 is greater than the diameter d2. The function of this diameter difference will be described in more detail below.

Two membranes 76, 78, which may consist in particular of silicone, are provided on the carrier element 60. By means of these membranes 76, 78, a pressure measurement can be carried out in the supply line 62 and the discharge line 64, as will be described in more detail below. Furthermore, the carrier element 60 has a further opening 80. This opening 80 is bridged only by the supply line 62. As can be seen in FIGS. 3 and 4, the supply line 62 has a further connector piece 82. By means of this connector piece 82, the supply tube 62 can be connected to a bag 84. The bag 84 contains flushing fluid. The bag 84 is fastened to a fastening hook 85 of the console 42. The supply line 62 further comprises a container 86 with an enlarged diameter. Said container 86 is located between the connector piece 82 and the carrier element 60. The container 86 can be fastened to a receptacle 88 on the console and abuts a console-side window 90. By means of this arrangement, a fill-level measurement of the supply line 62 can be provided for example by means of a capacitive sensor. The discharge line 64 also has a connector piece 92. The connector piece 92 can in this case be connected to a collection bag 94 for used flushing fluid. The collection bag 94 is also fastened to a fastening hook 95 of the console 42. The fastening hooks 85, 95 together with the bags 84, 94 are provided on opposite short sides of the console 42.

Figure 8:
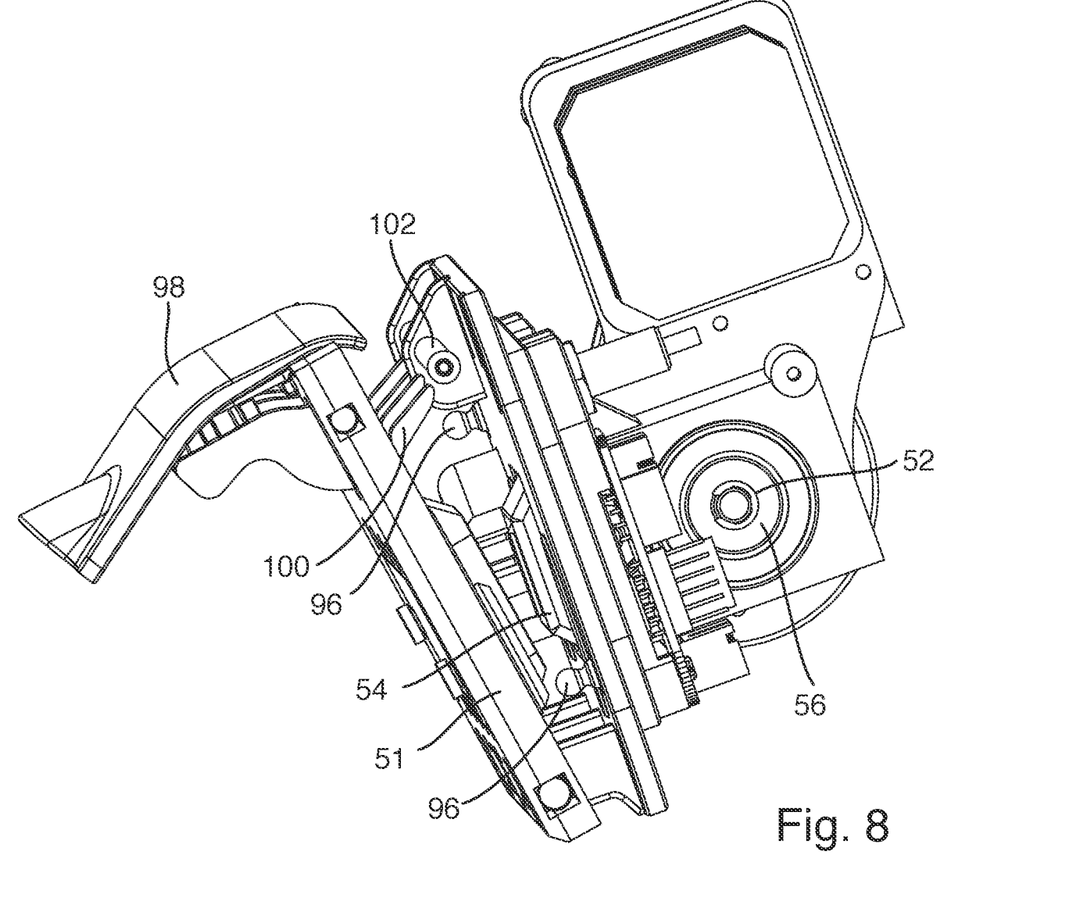
FIG. 8 is a schematic perspective view of the closing element of the console shown in FIGS. 3 and 4.

The console has a number of fixing bolts 96 for fastening the carrier element 60 in the receptacle 50. Once the carrier element 60 is arranged in the receptacle 50, the receptacle 50 can be closed, as shown in FIG. 3. For this purpose, the closing element 51 is transferred from the open position shown in FIG. 4 into its closed position shown in FIG. 3. In order to close the closing element 51, said element has a closing flap 98. The closing flap 98 can be seen particularly clearly in FIG. 8. This is pivotable. In order to close the closing element 51, the closing flap 98 is pivoted such that teeth 100 of the closing flap 98 engage behind a console-side fastening strip 102 such that the closing element 51 is securely closed in the closed position.

As can be seen from FIG. 3, the supply line 62 is guided into the console 42 on one side and guided out thereof on an opposite side. In contrast, the discharge line 64 is guided into and out of the console 42 on the same side, in particular on the side on which the discharge line 64 is guided out of the console 42 in the direction of the catheter pump 10. Accordingly, the discharge line 64 is guided in an arc (visible in FIG. 6) through the carrier element 60 such that the discharge line 64 has an arcuate section 69.

In order to push the supply line 62 and the discharge line 64 against the fingers 54 of the pump 52 in the closed position of the closing element 51, the closing element 51 has a pressing element 104, 106 for the supply line 62 and the discharge line 64 in each case. Said pressing elements 104, 106 can be clearly seen in FIG. 7. Said elements extend in each case along the pump sections 72, 74 and are pushed at the lateral ends by at least one spring element 108, 110 in each case against the fingers 54. As can be seen in FIG. 4, a cover 112 is arranged over the pressing elements 104, 106.

The closing element 51 also has a pushing element 114, 116 in each case, which can likewise be seen in FIG. 7, a compression spring 118, 120 also being provided here in each case. The pushing elements 114, 116 cooperate in this case with the membranes 66, 68 and console-side sensor elements 122, 124 (cf. FIG. 4) such that a pressure measurement is possible in the supply line 62 and in the discharge line 64. A console-side sensor element 126 and a closing-element-side strip 128, which act on the supply line 62 such that air bubble detection can be carried out, engage in the recess 80 in the carrier element 60 in the closed position. Indeed, as far as possible no air bubbles or other gas bubbles should be allowed through the supply line 62. Air bubble detection can in this case be carried out by means of optical methods or by means of capacitive measurement, for example.

The operation of the flushing system 40 is then as follows: First, the flushing system 40 is connected to the catheter pump 10 to form a catheter pump system. The connector 66 of the supply line 62 is connected to the connector 36 of the catheter pump in the process. Similarly, the connector 68 of the discharge line 64 is connected to the connector 38 of the catheter pump 10. The pump 52 can then be started. Thereafter, flushing fluid is supplied to the catheter 18 of the catheter pump 10 from the bag 84 via the supply line 62 and the tube 22. The flushing fluid can in this case consist of a 20% sterile glucose solution. Heparin may be added to the flushing fluid. The amount of flushing fluid can be set to 600-2,500 ml/24 h in operation, and approximately 12,000 ml/24 h when there is filling with a significantly larger flow.

Flushing fluid then flows through the catheter 10 in the distal direction. Some of the flushing fluid is then guided back through the catheter 18 in the proximal direction and acts as a lubricant for the rotor shaft 32 of the catheter 18. Furthermore, blood is effectively prevented from entering the catheter 18 by the flushing fluid. The used flushing fluid is then supplied to the collection bag 94 via the tube 24 and the return line 64. On account of the fact that the diameter d2 of the pump section 74 of the return line 64 is smaller than the diameter d1 of the pump section 72 of the supply line 62, the pump section 64 cooperates with the pump 52 as a throttle point. Thus, approximately one third of the flushing fluid pumped into the catheter 18 is pumped out of the catheter again, while two thirds of the flushing fluid enters the patient's circulation, with blood being prevented from entering the catheter 18 at the same time. Accordingly, the cross-sectional area of the diameter d2 of the pump section 74 of the return line 64 is also approximately only one third of the cross-sectional area with the diameter d1 of the pump section 72 of the supply line 62.

Each finger 54 of the pump 52 acts on the two pump sections 72 and 74 in the same way. The linear peristaltic pump 52 is a positive displacement pump in which the flushing fluid to be conveyed is forced through by external mechanical deformation of the lines 62, 64 or pump sections 72, 74 thereof, the compressed section of the pump sections 72, 74 "migrating" due to the sequential axial movement of the fingers 54. A pressure measurement is possible in the lines 62, 64 by means of the sensor elements 122, 124, while air bubble detection is possible in the supply line 62 by means of the sensor element 126.

The main functions of the console 42 are to monitor and control the rotational speed of the catheter pump 10 and the flow rate of the flushing fluid. The console 42 has two monitors on a broad face. The first monitor 130 serves as a main monitor and is designed as a touch screen. All control and monitoring parameters for the system are displayed on the monitor 130. An operating system, such as Windows, serves as an input system on the screen in this case. A separate operating system, which is specially designed for medical electronics, is used to control the catheter pump 10 and/or the flushing system 40. The control of the medical electronics is used in particular to control the rotational speed of the catheter pump 10 and the pump 52 of the flushing system 40. Should the monitor 130 fail for any reason, the console 42 has a second emergency monitor 132. This monitor has only a few functions, such as indicating the rotational speed of the catheter pump 10. By means of this so-called SUI (Safety User Interface), the operation of the catheter pump 10 and/or the flushing system 40 can only be terminated, but not started.

The invention claimed is:

1. A flushing system comprising:
a supply line having a supply line pump section;
a discharge line having a discharge line pump section, wherein the discharge line is separate from the supply line; and
a pump, wherein
a diameter d2 of the discharge line pump section of the discharge line is smaller than a diameter d1 of the supply line pump section of the supply line, in that the pump cooperates with the supply line pump section of the supply line, and in that the pump cooperates with the discharge line pump section of the discharge line, a carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow.

2. The flushing system according to claim 1, wherein the pump sections of the supply line and of the discharge line extend in parallel with one other and flushing fluid flows therethrough in opposite directions during operation.

3. The flushing system according to claim 2, further comprising:
an arcuate section, wherein
the supply line and/or the discharge line is/are coupled to or connected to said arcuate section,
the carrier element having a first side and a second side, and
the arcuate section extends through the carrier element such that the supply line and/or discharge line are guided into the first side of the carrier element and out of the first side of the carrier element.

4. The flushing system according to claim 3, wherein
a console having the pump is provided, and
the pump sections of the supply line and of the discharge line can be inserted into a receptacle in the console such that the pump can cooperate with the pump sections of the supply line and of the discharge line in order to convey fluid.

5. The flushing system according to claim 4, wherein
the carrier element together with the supply line and discharge line can be detachably placed on the console.

6. The flushing system according to claim 5, wherein
the console has a closing element for closing the receptacle, wherein the pump sections of the supply line and of the discharge line cooperate with the pump in order to convey fluid only when the closing element is in a closed position.

7. The flushing system according to claim 6, wherein
the closing element has a pressing element that presses the supply line and/or the discharge line against the camshaft system under preloading.

8. The flushing system according to claim 7, wherein
the pressing element is provided for the supply line and the discharge line in each case.

9. A system comprising:
a carrier element; and a flushing system, wherein
the flushing system including:
a supply line having a supply line pump section;
a discharge line having a discharge line pump section, wherein the discharge line is separate from the supply line;
a pump,
wherein a diameter d2 of the discharge line pump section of the discharge line is smaller than a diameter d1 of the supply line pump section of the supply line, in that the pump cooperates with the supply line pump section of the supply line, and in that the pump cooperates with the discharge line pump section of the discharge line, the carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow, wherein the pump sections of the supply line and of the discharge line extend in parallel with one other and flushing fluid flows therethrough in opposite directions during operation; and an arcuate section, wherein the supply line and/or the discharge line is/are coupled to or connected to said arcuate section, wherein the carrier element having a first side and a second side, wherein the arcuate section extends through the carrier element such that the supply line and/or discharge line are guided into the first side of the carrier element and out of the first side of the carrier element, wherein a console having the pump is provided, wherein the pump sections of the supply line and of the discharge line can be inserted into a receptacle in the console such that the pump can cooperate with the pump sections of the supply line and of the discharge line in order to convey fluid, wherein the carrier element together with the supply line and discharge line can be detachably placed on the console, wherein the console has a closing element for closing the receptacle, wherein the pump sections of the supply line and of the discharge line cooperate with the pump in order to convey fluid only when the closing element is in a closed position, wherein the closing element has a pressing element that presses the supply line and/or the discharge line against the camshaft system under preloading, wherein the pressing element is provided for the supply line and the discharge line in each case.

10. A system comprising:

a console; and a flushing system, the flushing system including:

a supply line having a supply line pump section;

a discharge line having a discharge line pump section;

a pump, wherein a diameter d2 of the discharge line pump section of the discharge line is smaller than a diameter d1 of the supply line pump section of the supply line, in that the pump cooperates with the supply line pump section of the supply line, and in that the pump cooperates with the discharge line pump section of the discharge line, a carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow, wherein the pump sections of the supply line and of the discharge line extend in parallel with one other and flushing fluid flows therethrough in opposite directions during operation; and an arcuate section, wherein the supply line and/or the discharge line is/are coupled to or connected to said arcuate section, wherein the carrier element having a first side and a second side, wherein the arcuate section extends through the carrier element such that the supply line and/or discharge line are guided into the first side of the carrier element and out of the first side of the carrier element, wherein the carrier element together with the supply line and discharge line can be detachably placed on the console, wherein the console has a closing element for closing the receptacle, wherein the pump sections of the supply line and of the discharge line cooperate with the pump in order to convey fluid only when the closing element is in a closed position, wherein the closing element has a pressing element that presses the supply line and/or the discharge line against the camshaft system under preloading, wherein the pressing element is provided for the supply line and the discharge line in each case, wherein the supply line and the discharge line are fastened to the carrier element, wherein the carrier element extends along the main extension plane, wherein the supply line and the discharge line extend through the carrier element in said main extension plane, wherein the carrier element has an opening, wherein the console has the pump and a receptacle for the carrier element, and wherein the pump sections of the supply line and of the discharge line can be inserted into the receptacle in such a way that the pump cooperates with the pump sections of the supply line and of the discharge line.

11. A catheter pump system comprising:

a console;

a catheter pump having a catheter and a flushing system, wherein the flushing system including:

a supply line having a supply line pump section;

a discharge line having a discharge line pump section;

a pump, wherein a diameter d2 of the discharge line pump section of the discharge line is smaller than a diameter d1 of the supply line pump section of the supply line, in that the pump cooperates with the supply line pump section of the supply line, and in that the pump cooperates with the discharge line pump section of the discharge line, a carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow, wherein the pump sections of the supply line and of the discharge line extend in parallel with one other and flushing fluid flows therethrough in opposite directions during operation; and an arcuate section, wherein the supply line and/or the discharge line is/are coupled to or connected to said arcuate section, wherein the carrier element having a first side and a second side, wherein the arcuate section extends through the carrier element such that the supply line and/or discharge line are guided into the first side of the carrier element and out of the first side of the carrier element, wherein the carrier element together with the supply line and discharge line can be detachably placed on the console, wherein the console has a closing element for closing the receptacle, wherein the pump sections of the supply line and of the discharge line cooperate with the pump in order to convey fluid only when the closing element is in a closed position, wherein the closing element has a pressing element that presses the supply line and/or the discharge line against the camshaft system under preloading, wherein the pressing element is provided for the supply line and the discharge line in each case, wherein the supply line and the discharge line are fastened to the carrier element, wherein the carrier element extends along the main extension plane, wherein the supply line and the discharge line extend through the carrier element in said main extension plane, wherein the carrier element has an opening, wherein the console has the pump and a receptacle for the carrier element, and wherein the pump sections of the supply line and of the discharge line can be inserted into the receptacle in such a way that the pump cooperates with the pump sections of the supply line and of the discharge line, and wherein the supply line and the discharge line are fluidically connected to the catheter.

12. The flushing system according to claim 1, further comprising:

an arcuate section, wherein the supply line and/or the discharge line are coupled to or connected to said arcuate section, the carrier element having a first side and a second side, and the arcuate section extends through the carrier element such that the supply line and/or discharge line are guided into the first side of the carrier element and out of the first side of the carrier element.

13. The flushing system according to claim 1, wherein a console having the pump is provided, the pump sections of the supply line and of the discharge line can be inserted into a receptacle in the console such that the pump can cooperate with the pump sections of the supply line and of the discharge line in order to convey fluid.

14. The flushing system according to claim 2, wherein a console having the pump is provided, the pump sections of the supply line and of the discharge line can be inserted into a receptacle in the console such that the pump can cooperate with the pump sections of the supply line and of the discharge line in order to convey fluid.

15. The flushing system according to claim 4, wherein the console has a closing element for closing the receptacle, wherein the pump sections of the supply line and of the discharge line cooperate with the pump in order to convey fluid only when the closing is in a closed position.

16. A system comprising:

a carrier element for a flushing system, wherein the flushing system including:

a supply line having a supply line pump section;

a discharge line having a discharge line pump section, wherein the discharge line is separate from the supply line; and a pump, wherein a diameter $d2$ of the discharge line pump section of the discharge line is smaller than a diameter $d1$ of the supply line pump section of the supply line, in that the pump cooperates with the supply line pump section of the supply line, and in that the pump cooperates with the discharge line pump section of the discharge line, the carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow.

17. A system comprising:

a console; and a flushing system, wherein the flushing system includes:

a supply line having a supply line pump section;

a discharge line having a discharge line pump section; and a pump, wherein a diameter $d2$ of the discharge line pump section of the discharge line is smaller than a diameter $d1$ of the supply line pump section of the supply line, in that the pump cooperates with the supply line pump section of the supply line, and in that the pump cooperates with the discharge line pump section of the discharge line, a carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow, wherein the pump sections of the supply line and of the discharge line extend in parallel with one other and flushing fluid flows therethrough in opposite directions during operation; and an arcuate section, wherein the supply line and/or the discharge line is/are coupled to or connected to said arcuate section, wherein the carrier element having a first side and a second side, wherein the arcuate section extends through the carrier element such that the supply line and/or discharge line are guided into the first side of the carrier element and out of the first side of the carrier element, wherein the carrier element together with the supply line and discharge line can be detachably placed on the console, wherein the console has a closing element for closing the receptacle, wherein the pump sections of the supply line and of the discharge line cooperate with the pump in order to convey fluid only when the closing element is in a closed position, the closing element has a pressing element that presses the supply line and/or the discharge line against the camshaft system under preloading, wherein the console has the pump and a receptacle for the carrier element, and the pump sections of the supply line and of the discharge line can be inserted into the receptacle in such a way that the pump cooperates with the pump sections of the supply line and of the discharge line.

18. A system comprising:
a console; and a flushing system, wherein
the flushing system includes:
a supply line having a supply line pump section;
a discharge line having a discharge line pump section; and
a pump,
wherein a diameter d2 of the discharge line pump section of the discharge line is smaller than a diameter d1 of the supply line pump section of the supply line, in that the pump cooperates with the supply line pump section of the supply line, and in that the pump cooperates with the discharge line pump section of the discharge line, a carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow, wherein the pump sections of the supply line and of the discharge line extend in parallel with one other and flushing fluid flows therethrough in opposite directions during operation; and an arcuate section, wherein the supply line and/or the discharge line is/are coupled to or connected to said arcuate section, wherein the carrier element having a first side and a second side, wherein the arcuate section extends through the carrier element such that the supply line and/or discharge line are guided into the first side of the carrier element and out of the first side of the carrier element, wherein the carrier element together with the supply line and discharge line can be detachably placed on the console, wherein the console has a closing element for closing the receptacle, wherein the pump sections of the supply line and of the discharge line cooperate with the pump in order to convey fluid only when the closing element is in a closed position, the closing element has a pressing element that presses the supply line and/or the discharge line against the camshaft system under preloading, the pressing element is provided for the supply line and the discharge line in each case, the console has the pump and a receptacle for the carrier element, and the pump sections of the supply line and of the discharge line can be inserted into the receptacle in such a way that the pump cooperates with the pump sections of the supply line and of the discharge line.

19. A system comprising:
a flushing system including:
a supply line having a supply line pump section;
a discharge line having a discharge line pump section; and
a pump;
wherein a diameter d2 of the discharge line pump section of the discharge line is smaller than a diameter d1 of the supply line pump section of the supply line, in that the pump cooperates with the supply line pump section of the supply line, and in that the pump cooperates with the discharge line pump section of the discharge line, a carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow;

a catheter pump system including:
a catheter pump having a catheter and the flushing system wherein
the supply line and the discharge line are fluidically connected to the catheter.

20. A carrier element for a flushing system,
the flushing system comprising:
a supply line having a supply line pump section;
a discharge line having a discharge line pump section;
a pump;
wherein a diameter d2 of the discharge line pump section of the discharge line is smaller than a diameter d1 of the supply line pump section of the supply line, in that the pump cooperates with the supply line pump section of the supply line, and in that the pump cooperates with the discharge line pump section of the discharge line, a carrier element being provided to which the supply line and the discharge line are fastened, the carrier element extending along a main extension plane, the supply line and discharge line extending through the carrier element in said main extension plane, the carrier element having an opening, and the pump sections of the supply line and of the discharge line extending along the opening, the pump being designed as a linear peristaltic pump, the pump having a camshaft system, the camshaft system cooperating with the supply line and the discharge line in order to convey fluid, and the camshaft system sequentially compressing the supply line and the discharge line to generate a fluid flow, wherein the pump sections of the supply line and of the discharge line extend in parallel with one other and flushing fluid flows therethrough in opposite directions during operation; and an arcuate section, wherein the supply line and/or the discharge line is/are coupled to or connected to said arcuate section, wherein the carrier element having a first side and a second side, wherein the arcuate section extends through the carrier element such that the supply line and/or discharge line are guided into the first side of the carrier element and out of the first side of the carrier element, wherein the carrier element together with the supply line and discharge line can be detachably placed on the console, wherein the console has a closing element for closing the receptacle, wherein the pump sections of the supply line and of the discharge line cooperate with the pump in order to convey fluid only when the closing element is in a closed position, wherein the closing element has a pressing element that presses the supply line and/or the discharge line against the camshaft system under preloading, wherein the pressing element is provided for the supply line and the discharge line in each case, wherein the supply line and the discharge line are fastened to the carrier element, wherein the carrier element extends along a main extension plane, wherein the supply line and the discharge line extend through the carrier element in said main extension plane, wherein the carrier element has an opening, wherein the console has a pump and a receptacle for the carrier element, and wherein the pump sections of the supply line and of the discharge line can be inserted into the receptacle in such a way that the pump cooperates with the pump sections of the supply line and of the discharge line.

\* \* \* \* \*